United States Patent [19]
Winters

[11] Patent Number: 5,178,608
[45] Date of Patent: Jan. 12, 1993

[54] BALLOON CATHETER WITH EXPANDABLE INFLATION MEMBER

[75] Inventor: R. Edward Winters, Andover, Mass.

[73] Assignee: Advanced Biomedical Devices, Inc., Lawrence, Mass.

[21] Appl. No.: 586,994

[22] Filed: Sep. 24, 1990

[51] Int. Cl.$^5$ .......................................... A61M 29/00
[52] U.S. Cl. .................................. 604/99; 604/101; 606/192
[58] Field of Search ................. 604/96, 101, 102, 164, 604/165, 167, 99; 606/192, 194

[56] References Cited

U.S. PATENT DOCUMENTS

| | | | |
|---|---|---|---|
| 3,402,717 | 9/1968 | Doherty | 604/99 |
| 4,655,746 | 4/1987 | Daniels et al. | 604/101 |
| 4,708,718 | 11/1987 | Daniels | 604/53 |
| 4,832,028 | 5/1989 | Patel | 604/101 |
| 4,846,174 | 7/1989 | Willard et al. | 604/96 |
| 4,911,163 | 3/1990 | Fina | 604/101 |
| 4,950,239 | 8/1990 | Gahara et al. | 604/96 |

FOREIGN PATENT DOCUMENTS

| | | | |
|---|---|---|---|
| 8606285 | 11/1986 | World Int. Prop. O. | 606/194 |
| 8907413 | 8/1989 | World Int. Prop. O. | 604/96 |

Primary Examiner—John D. Yasko
Assistant Examiner—Anthony Gutowski
Attorney, Agent, or Firm—Stephen G. Matzuk

[57] ABSTRACT

A single lumen catheter used alone or in multiples of various diameters in a coaxial disposition over a guidewire or catheter having a means to occlude the distal opening of the single lumen catheter. Each single lumen catheter includes a flexible tube and a balloon disposed about the exterior of the single lumen catheter near the distal end, and a opening in the tube to permit fluid communication into the balloon from the interior of the single lumen catheter. Alternate embodiments include an interior fluted collar upon which the balloon of the inner catheter abuts, forming an orifice providing a selected fluid flow into the catheter. Thus, the single lumen catheters provide a steerable guidewire system having a greater selection of catheters without requiring an inner lumen.

5 Claims, 1 Drawing Sheet

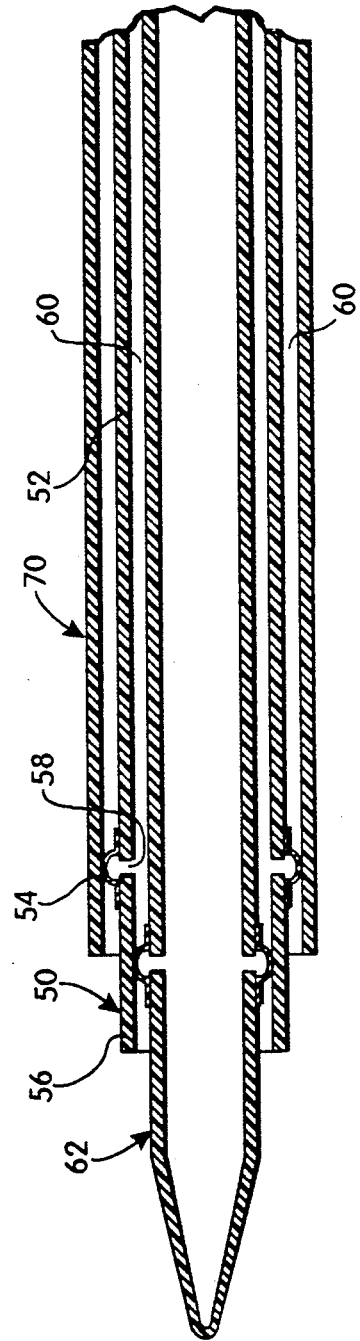
Fig. 1
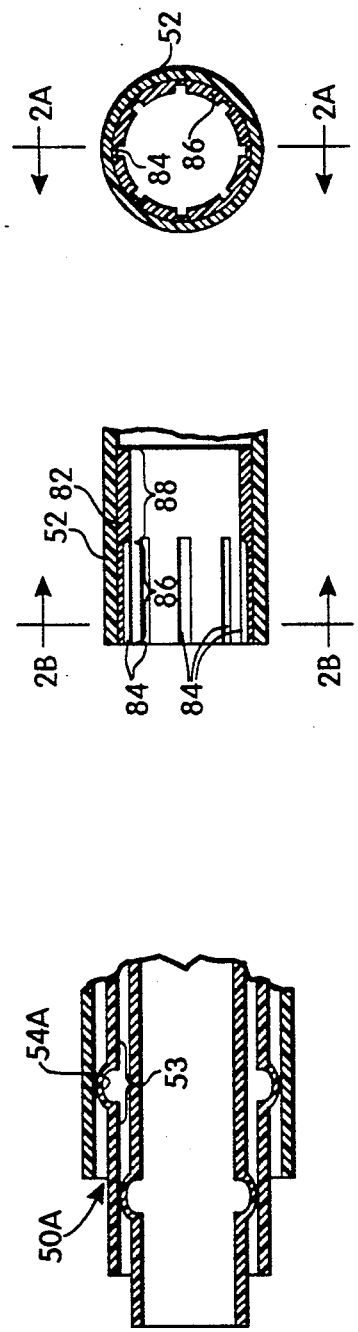
Fig. 2B
Fig. 2A
Fig. 1A

BALLOON CATHETER WITH EXPANDABLE INFLATION MEMBER

Field of the Invention

The present invention relates to catheters, and in particular flexible catheters used in the treatment and diagnosis of vascular disease.

BACKGROUND OF THE INVENTION

Catheters vary in construction and materials, such as providing a wire braid reinforced lumen or an inner lumen of greater rigidity than the outer lumen. Similarly, catheters vary in size from a few French (1 French=0.013 inch) to 50 French. Steerable catheters, unlike diagnostic catheters, generally do not have any reinforcement to provide torque characteristics. As such, steerable catheters are guided into the vasculature and to the area of interest in the vasculature over steerable guidewires which possess the necessary rigidity to transfer torque.

Access to the vasculature of interest is impaired due to the tortuous pathways and the small diameter vessels encountered. Furthermore, the application of radiopaque dye for diagnosis, and insertion of balloon and laser appliances for unblocking obstructions require the positioning of atraumatic and/or steerable elements for location of the area of interest. Such diverse requirements leads to the creation of complex catheter/guidewire structures. However, the need to reach the small diameter vessels results in a catheter structure limited to a specific function, and is often constructed in a manner which prohibits the exchange of guidewire or other coaxially related structure at the vessel site without complete withdrawal of the catheter. Furthermore, similar limitations with respect to the deployment of the guidewire exists, such that existing structures discourage guidewire or catheter exchanges while the other remains in place. For instance, guidewires having a balloon at the distal end are initially applied to reach and pre-dilate lesions, withdrawn and followed by the insertion of a balloon catheter to complete the dilation. Such structural limitation actively discourage complete therapy and introduce significant procedural complications and/or risk to the patient.

SUMMARY OF THE INVENTION

A single lumen catheter is provided which is used alone or in concentrically disposed multiples of a central guidewire, to provide diverse diagnostic and therapeutic functions while permitting free exchange of one or more of the assembled structural elements without removal of the selected guidewire or catheter element. The single lumen catheter typically comprises a flexible tube having a balloon mounted thereon near the distal end and an aperture to provide fluid access to the balloon from the interior of the single lumen catheter. The single lumen catheter is typically applied over a smaller structure such as a guidewire having the ability to occlude the distal opening of the single lumen guidewire to contain the fluid to be introduced into the balloon. By example, a balloon guidewire as described in U.S. patent application Ser. No. 07/454,411 by the present inventor and incorporated by reference herein, provides a balloon closure of the single lumen guidewire distal opening by inflating the guidewire balloon. Similarly, additional single lumen catheters may be applied over the previously inserted single lumen catheter which, by inflating its balloon, occludes the overapplied single lumen catheter.

Further embodiments of the present invention include the addition of an internal collar having selected fluted passages formed therein and upon which the sealing member of the included structure (e.g. balloon) seats, forming an orifice of reduced diameter to selectively meter fluid into the vessel.

BRIEF DESCRIPTION OF THE DRAWING

These and further features of the present invention will be better understood by reading the following Detailed Description, taken together with the Drawing, wherein:

FIG. 1 is a cross-section view of one embodiment of the present invention;

FIG. 1A is a cross-section view of an alternate embodiment of the catheter of FIG. 1A;

FIG. 2A is a cross-section of a portion of an alternate embodiment of the present invention; and FIG. 2B is an end-view of an element of the embodiment of FIG. 2A.

DETAILED DESCRIPTION OF THE INVENTION

One embodiment 50 of the single lumen catheter according to the present invention is shown in FIG. 1, comprising a flexible tube 52 of a selectably semi-rigid material such as polyamid, PVC or polyurathane, a balloon 54 near the distal end 56 of the tube 52 expandable by the infusion of fluid through the aperture 58 from the interior 60 of the tube 52. The balloon may also be recessed to be flush with the exterior surface of the tube 52 when uninflated. Typically, the single lumen catheter is applied over an elongated member 62, such as the balloon guidewire of co-pending patent application Ser. No. 07/454,411, or other structure adapted to receive the single lumen catheter 50 and selectively provide a substantially complete occlusion of the distal end 52 of the interior 60 of the single lumen catheter 50, allowing the balloon to be inflated to provide the desired therapy such as angioplasty.

Alternately as shown in FIG. 1A, the entire catheter 50A may be of balloon material having the expandable portion 54A of the balloon material limited to a preferred balloon area 53, wherein the remaining length of the catheter is unexpanded by the application of interior 60 fluid pressure.

The present invention also envisions a compound structure wherein additional concentric single lumen catheters are applied. A single additional single lumen catheter 70 is shown in FIG. 1, and is engaged by balloon 54 of the inner single lumen catheter 50. According to this embodiment, there is no inherent limit to the number or diameter of additional catheters, or requirement that they be applied in any sequence, e.g. applied between previously inserted catheters.

A further inventive feature of the present invention is illustrated in FIG. 2A and FIG. 2B, wherein a close fitting annular inner tip member 82 is disposed between the distal end 56 and the aperture 58 of the tube 52. The annular member has a thickness at least equal to the depth of the channels 84 of the first portion 86 of the annular member 82. A second portion 88 of the annular member 82 comprises a substantially smooth surface to provide substantially complete occlusion of the interior 60 of the tube when a balloon (or equivalent) is seated thereon. Thus, the present invention provides complete flow inhibition (88) or selected flow (86) by axial placement of the sealing member (e.g. guidewire balloon) on selected portions of the annular member 82. Moreover the channels may include axially extending holes.

Modifications and substitutions of the present invention by one of ordinary skill in the art is considered to be within the scope of the present invention, which is not to be limited except by the claims which follow.

What is claimed is:

1. A catheter comprising:
   a flexible tube having an open distal and a proximal end; and
   a balloon portion near the distal end; and
   an expandable diameter elongated member disposed within said flexible tube, wherein
   said flexible tube includes a longitudinal aperture in said tube permitting fluid communication therethrough and to receive said expandable diameter elongated member and a radial aperture permitting fluid communication between said longitudinal aperture and the interior of said balloon, and wherein
   said flexible tube is adapted to be engaged by the expanded diameter of the elongated member when disposed thereon to provide a selectively occluded fluid path between the exterior of said elongated member and the interior of said flexible tube.

2. The catheter of claim 1, further comprising
   an annular member disposed within and retained by said flexible tube between the distal end and the radially disposed aperture, said annular member having an interior wall including at least one channel axially disposed thereon, whereupon engagement of said annular member by the expanded diameter of the elongated diameter member, the fluid path through said annular member within said interior wall is substantially occluded and a selected fluid path from the proximal to the open distal end of the flexible tube longitudinal aperture is formed according to said channel.

3. The catheter of claim 1, wherein the flexible tube comprises at least a portion of expandable balloon material.

4. The catheter of claim 3, wherein said expandable balloon material portion has a reduced cross-section near the distal end of said flexible tube, providing a balloon portion and an unexpanded section of tubing between the distal end and said balloon portion.

5. The catheter of claim 1, wherein the flexible tube comprises a semi-rigid material comprising one of polyamide, PVC an polyurathane, and said balloon portion comprises a balloon mounted on said flexible tube in fluid communication with said selectively occluded fluid path.

* * * * *